(12) United States Patent
Carley (10) Patent No.: US 8,801,691 B2
(45) Date of Patent: *Aug. 12, 2014

(54) DELIVERY AND EXCHANGE CATHETER FOR STORING GUIDEWIRE

(75) Inventor: Mike Carley, San Jose, CA (US)

(73) Assignee: Revascular Therapeutics, Inc., Sunnyvale, CA (US)

( * ) Notice: Subject to any disclaimer, the term of this patent is extended or adjusted under 35 U.S.C. 154(b) by 117 days.

This patent is subject to a terminal disclaimer.

(21) Appl. No.: 13/453,304

(22) Filed: Apr. 23, 2012

(65) Prior Publication Data

US 2012/0209302 A1    Aug. 16, 2012

Related U.S. Application Data

(63) Continuation of application No. 12/623,198, filed on Nov. 20, 2009, now Pat. No. 8,162,891.

(60) Provisional application No. 61/118,260, filed on Nov. 26, 2008.

(51) Int. Cl.
*A61M 31/00* (2006.01)
*A61M 5/178* (2006.01)

(52) U.S. Cl.
USPC ..................... 604/508; 604/164.13

(58) Field of Classification Search
CPC .............. A61M 25/0071; A61M 25/0026; A61M 2025/0681; A61M 2025/0175; A61M 2039/082; A61M 25/0015; A61M 25/0169; A61M 25/0172; A61M 2025/0079; A61M 2039/0235; A61M 25/0104; A61M 25/09; A61M 25/09016; A61M 25/09025; A61M 25/09033; A61M 25/09041; A61M 25/0905; A61B 17/22; A61B 17/3207; A61B 17/00234; A61B 17/320758; A61B 2017/22044; A61B 2017/22042

See application file for complete search history.

(56) References Cited

U.S. PATENT DOCUMENTS

| | | |
|---|---|---|
| 4,068,660 A | 1/1978 | Beck |
| 4,149,535 A | 4/1979 | Volder |
| 4,368,730 A | 1/1983 | Sharrock |
| 4,377,169 A | 3/1983 | Banks |
| 4,445,509 A | 5/1984 | Auth et al. |
| 4,471,779 A | 9/1984 | Antoshkiw et al. |
| 4,490,421 A | 12/1984 | Levy |
| 4,516,972 A | 5/1985 | Samson |
| 4,534,363 A | 8/1985 | Gold et al. |
| 4,538,622 A | 9/1985 | Samson et al. |
| 4,545,390 A | 10/1985 | Leary |
| 4,548,206 A | 10/1985 | Osborne |

(Continued)

FOREIGN PATENT DOCUMENTS

| | | |
|---|---|---|
| WO | 9211055 A1 | 7/1992 |
| WO | 0169998 A1 | 9/2001 |

OTHER PUBLICATIONS

"Low Cost Monolithic Voltage-to-Frequency Converter;" (product AD654 description); Analog Devices, Dec. 1999, pp. 1-11.

*Primary Examiner* — Manuel Mendez
(74) *Attorney, Agent, or Firm* — Seager, Tufte & Wickhem, LLC (57) ABSTRACT

A support catheter for stowing and exchanging guidewires and other working elements comprises a catheter body having a proximal region and a distal region. A single, contiguous lumen is formed from the proximal region through the distal region and has a larger proximal cross-sectional area than distal cross-sectional area.

13 Claims, 5 Drawing Sheets

(56) References Cited

U.S. PATENT DOCUMENTS

| | | |
|---|---|---|
| 4,554,929 A | 11/1985 | Samson et al. |
| 4,573,470 A | 3/1986 | Samson et al. |
| 4,586,923 A | 5/1986 | Gould et al. |
| 4,601,705 A | 7/1986 | McCoy et al. |
| 4,613,385 A | 9/1986 | Thomas et al. |
| 4,616,653 A | 10/1986 | Samson et al. |
| 4,619,263 A | 10/1986 | Frisbie et al. |
| 4,641,654 A | 2/1987 | Samson et al. |
| 4,646,719 A | 3/1987 | Neuman et al. |
| 4,646,736 A | 3/1987 | Auth et al. |
| 4,646,742 A | 3/1987 | Packard et al. |
| 4,676,249 A | 6/1987 | Arenas et al. |
| 4,708,717 A | 11/1987 | Deane et al. |
| 4,708,718 A | 11/1987 | Daniels et al. |
| 4,715,378 A | 12/1987 | Pope et al. |
| 4,717,387 A | 1/1988 | Inoue et al. |
| 4,719,924 A | 1/1988 | Crittenden et al. |
| 4,721,117 A | 1/1988 | Mar et al. |
| 4,723,936 A | 2/1988 | Buchbinder et al. |
| 4,739,768 A | 4/1988 | Engelson |
| 4,763,647 A | 8/1988 | Gambale |
| 4,767,400 A | 8/1988 | Miller et al. |
| 4,779,628 A | 10/1988 | Machek |
| 4,781,486 A | 11/1988 | Mochizuki |
| 4,798,598 A | 1/1989 | Bonello et al. |
| 4,820,288 A | 4/1989 | Isono |
| 4,832,047 A | 5/1989 | Sepetka et al. |
| 4,846,186 A | 7/1989 | Box et al. |
| 4,899,787 A | 2/1990 | Ouchi et al. |
| 4,906,241 A | 3/1990 | Noddin et al. |
| 4,923,462 A | 5/1990 | Stevens et al. |
| 4,925,445 A | 5/1990 | Sakamoto et al. |
| 4,926,858 A | 5/1990 | Gifford et al. |
| 4,940,062 A | 7/1990 | Hampton et al. |
| 4,946,466 A | 8/1990 | Pinchuk et al. |
| 4,953,553 A | 9/1990 | Tremulis |
| 4,979,939 A | 12/1990 | Shiber et al. |
| 4,990,134 A | 2/1991 | Auth |
| 5,021,044 A | 6/1991 | Sharkawy |
| 5,030,204 A | 7/1991 | Badger et al. |
| 5,041,082 A | 8/1991 | Shiber |
| 5,041,085 A | 8/1991 | Osborne et al. |
| 5,059,851 A | 10/1991 | Corl et al. |
| 5,060,660 A | 10/1991 | Gambale et al. |
| 5,067,489 A | 11/1991 | Lind |
| 5,107,852 A | 4/1992 | Davidson et al. |
| 5,115,814 A | 5/1992 | Griffith et al. |
| 5,116,350 A | 5/1992 | Stevens |
| 5,144,959 A | 9/1992 | Gambale et al. |
| 5,156,157 A | 10/1992 | Valenta et al. |
| 5,165,421 A | 11/1992 | Fleischhacker et al. |
| 5,174,276 A | 12/1992 | Crockard |
| 5,176,661 A | 1/1993 | Evard et al. |
| 5,178,158 A | 1/1993 | De Toledo et al. |
| 5,184,627 A | 2/1993 | de Toledo |
| 5,195,954 A | 3/1993 | Schnepp-Pesch |
| 5,195,971 A | 3/1993 | Sirhan et al. |
| 5,203,338 A * | 4/1993 | Jang ............................ 600/463 |
| 5,209,727 A | 5/1993 | Radisch et al. |
| 5,211,636 A | 5/1993 | Mische |
| 5,217,482 A | 6/1993 | Keith et al. |
| 5,250,034 A | 10/1993 | Appling et al. |
| 5,263,959 A | 11/1993 | Fischell et al. |
| 5,267,979 A | 12/1993 | Appling et al. |
| RE34,556 E | 3/1994 | Sjostrom |
| 5,304,131 A | 4/1994 | Paskar et al. |
| 5,306,252 A | 4/1994 | Yutori et al. |
| 5,314,438 A | 5/1994 | Shturman et al. |
| 5,345,945 A | 9/1994 | Hodgson et al. |
| 5,346,473 A | 9/1994 | Bowman |
| 5,348,017 A | 9/1994 | Thornton et al. |
| 5,358,485 A | 10/1994 | Vance |
| 5,366,464 A | 11/1994 | Belknap |
| 5,368,035 A | 11/1994 | Hamm et al. |
| 5,372,602 A | 12/1994 | Burke et al. |
| 5,377,690 A | 1/1995 | Berthiaume |
| 5,378,234 A | 1/1995 | Hammerslag et al. |
| 5,381,782 A | 1/1995 | DeLaRama et al. |
| 5,391,147 A | 2/1995 | Imran et al. |
| 5,427,118 A * | 6/1995 | Nita et al. ...................... 600/585 |
| 5,456,667 A | 10/1995 | Ham et al. |
| 5,462,523 A | 10/1995 | Samson et al. |
| 5,476,473 A | 12/1995 | Heckele et al. |
| 5,484,407 A | 1/1996 | Osypka |
| 5,507,738 A | 4/1996 | Ciervo |
| 5,510,070 A | 4/1996 | Krause et al. |
| 5,527,298 A | 6/1996 | Vance et al. |
| 5,527,326 A | 6/1996 | Hermann et al. |
| 5,531,677 A | 7/1996 | Lundquist et al. |
| 5,540,707 A | 7/1996 | Ressemann et al. |
| 5,563,482 A | 10/1996 | Shaw et al. |
| 5,569,197 A | 10/1996 | Helmus et al. |
| 5,571,085 A | 11/1996 | Accisano |
| 5,571,086 A * | 11/1996 | Kaplan et al. ............... 604/96.01 |
| 5,591,142 A | 1/1997 | Van Erp et al. |
| 5,606,981 A | 3/1997 | Tartacower et al. |
| 5,611,777 A | 3/1997 | Bowden et al. |
| 5,624,396 A | 4/1997 | McNamara et al. |
| 5,632,755 A | 5/1997 | Nordgren et al. |
| 5,651,785 A | 7/1997 | Abela et al. |
| 5,657,000 A | 8/1997 | Ellingboe et al. |
| 5,662,671 A | 9/1997 | Barbut et al. |
| 5,663,886 A | 9/1997 | Lueck et al. |
| 5,665,533 A | 9/1997 | Hoepfl et al. |
| 5,672,945 A | 9/1997 | Krause et al. |
| 5,681,336 A | 10/1997 | Clement et al. |
| 5,689,194 A | 11/1997 | Richards et al. |
| 5,702,373 A | 12/1997 | Samson et al. |
| 5,766,016 A | 6/1998 | Sinclair et al. |
| 5,772,609 A | 6/1998 | Nguyen et al. |
| 5,776,114 A | 7/1998 | Frantzen et al. |
| 5,820,591 A | 10/1998 | Thompson et al. |
| 5,820,592 A | 10/1998 | Hammerslag et al. |
| 5,843,103 A | 12/1998 | Wulfman |
| 5,848,986 A | 12/1998 | Lundquist et al. |
| 5,860,923 A | 1/1999 | Lenker et al. |
| 5,860,938 A | 1/1999 | Lafontaine et al. |
| 5,865,800 A | 2/1999 | Mirarchi et al. |
| 5,868,685 A | 2/1999 | Powell et al. |
| 5,897,567 A | 4/1999 | Ressemann et al. |
| 5,908,395 A | 6/1999 | Stalker et al. |
| 5,922,003 A | 7/1999 | Anctil et al. |
| 5,976,093 A | 11/1999 | Jang et al. |
| 5,997,523 A | 12/1999 | Jang et al. |
| 6,001,112 A | 12/1999 | Taylor et al. |
| 6,022,336 A | 2/2000 | Zadno et al. |
| 6,050,972 A | 4/2000 | Zadno et al. |
| 6,053,903 A | 4/2000 | Samson et al. |
| 6,056,743 A | 5/2000 | Ellis et al. |
| 6,059,767 A | 5/2000 | Noriega |
| 6,066,149 A | 5/2000 | Samson et al. |
| 6,068,623 A | 5/2000 | Zadno-Azizi et al. |
| 6,093,157 A | 7/2000 | Chandrasekaran et al. |
| 6,106,487 A | 8/2000 | Duane et al. |
| 6,120,515 A | 9/2000 | Rogers et al. |
| 6,143,009 A | 11/2000 | Shiber et al. |
| 6,152,909 A | 11/2000 | Bagaoisan et al. |
| 6,156,046 A | 12/2000 | Passafaro et al. |
| 6,179,851 B1 | 1/2001 | Barbut et al. |
| 6,183,432 B1 | 2/2001 | Milo |
| 6,217,567 B1 | 4/2001 | Zadno-Azizi et al. |
| 6,234,971 B1 | 5/2001 | Jang |
| 6,258,052 B1 | 7/2001 | Milo |
| 6,299,622 B1 | 10/2001 | Snow et al. |
| 6,312,438 B1 | 11/2001 | Adams |
| 6,355,014 B1 | 3/2002 | Zadno-Azizi et al. |
| 6,375,628 B1 | 4/2002 | Zadno-Azizi et al. |
| 6,387,109 B1 | 5/2002 | Davison et al. |
| 6,482,217 B1 | 11/2002 | Pintor et al. |
| 6,482,221 B1 | 11/2002 | Hebert et al. |
| 6,500,130 B2 | 12/2002 | Kinsella et al. |
| 6,533,749 B1 | 3/2003 | Mitusina et al. |
| 6,551,270 B1 | 4/2003 | Bimbo et al. |
| 6,585,717 B1 | 7/2003 | Wittenberger et al. |

(56) References Cited

U.S. PATENT DOCUMENTS

| | | |
|---|---|---|
| 6,602,264 B1 | 8/2003 | McGuckin, Jr. |
| 6,652,508 B2 | 11/2003 | Griffin et al. |
| 6,730,037 B2 | 5/2004 | Jang |
| 6,743,208 B1 | 6/2004 | Coyle |
| 6,746,411 B2 | 6/2004 | Khaw |
| 6,746,422 B1 | 6/2004 | Noriega et al. |
| 6,824,550 B1 | 11/2004 | Noriega et al. |
| 7,018,358 B2 | 3/2006 | Joergensen et al. |
| 7,107,096 B2 | 9/2006 | Fischell et al. |
| 7,160,724 B2 | 1/2007 | Sanberg et al. |
| 7,381,198 B2 | 6/2008 | Noriega et al. |
| 7,479,147 B2 | 1/2009 | Honeycutt et al. |
| 7,628,763 B2 | 12/2009 | Noriega et al. |
| 7,753,901 B2 | 7/2010 | Piskun et al. |
| 8,162,891 B2 * | 4/2012 | Carley .................... 604/164.13 |
| 2003/0015977 A1 | 1/2003 | Lee et al. |
| 2004/0102719 A1 | 5/2004 | Keith et al. |
| 2005/0020974 A1 | 1/2005 | Noriega et al. |
| 2005/0119615 A1 | 6/2005 | Noriega et al. |
| 2005/0228418 A1 | 10/2005 | Noriega et al. |
| 2005/0245962 A1 | 11/2005 | Adams et al. |
| 2006/0074442 A1 | 4/2006 | Noriega et al. |
| 2006/0241519 A1 | 10/2006 | Hojeibane et al. |
| 2006/0259052 A1 | 11/2006 | Pintor et al. |
| 2007/0175949 A1 | 8/2007 | Shelton et al. |
| 2007/0225615 A1 | 9/2007 | Chechelski et al. |
| 2007/0239140 A1 | 10/2007 | Chechelski et al. |
| 2008/0140101 A1 | 6/2008 | Carley et al. |
| 2008/0154345 A1 | 6/2008 | Taylor |
| 2008/0172033 A1 | 7/2008 | Keith et al. |
| 2008/0221601 A1 | 9/2008 | Huynh et al. |

* cited by examiner

DELIVERY AND EXCHANGE CATHETER FOR STORING GUIDEWIRE

CROSS-REFERENCES TO RELATED APPLICATIONS

This application is a continuation of U.S. patent application Ser. No. 12/623,198, filed on Nov. 20, 2009, which claims priority to U.S. Provisional Patent Application No. 61/118,260 filed Nov. 26, 2008. The entire disclosures of which are incorporated herein by reference.

BACKGROUND

1. Field of the Invention

The present invention relates generally to medical devices and methods. More particularly, the present invention relates to an intraluminal catheter configured to stow two or more treatment catheters and/or guidewires and allow for distal advancement of one such catheter or guidewire at a time.

The use of a dual lumen catheter for introducing and exchanging guidewires and therapeutic or imaging catheters has been proposed. See, for example, U.S. Pat. No. 5,203,338 and U.S. Patent Publication No. 2008/0154345. The systems described in each of these documents use an outer catheter or sheath having two proximal lumens connected to a single reduced-diameter distal lumen for delivering and exchanging guidewires, therapeutic catheters, and imaging catheters. Typically, a single guidewire is stored in one proximal lumen while a single imaging or therapeutic catheter is stored in the other proximal lumen. The dual lumen catheter may be positioned at a target site within the vasculature of the body lumen, and the guidewire and catheter selectively advanced through the distal lumen when needed.

While effective, the use of such storage catheters having two lumens in the proximal section is disadvantageous in several respects. First, the formation of two or more discrete lumens in the proximal portion usually results in a larger diameter. While acceptable in many applications, in some vascular and cardiovascular applications, it is desirable to reduce even the proximal diameter as much as possible. Second, the need to fabricate two or more discrete lumens in the proximal portion complicates the fabrication of the catheter. Additionally, the initial formation of discrete proximal lumens with fixed dimensions limits the ability to introduce therapeutic and imaging catheters which exceed the fixed dimensions.

For these reasons, it would be desirable to provide storage and exchange catheters which have reduced profile proximal portions, which are easier to fabricate, and which permit increased flexibility in the range of catheters and guidewires which be stored and selectively introduced. At least some of these objectives will be met by the inventions described and claimed below.

2. Description of the Background Art

U.S. Pat. Nos. 5,203,338; 5,665,533; 5,976,093; 5,997,523; 6,234,971; 6,730,037; 7,160,724; and WO 01/66698 and WO 92/11055 describe dual lumen catheters for holding and exchanging a guidewire and an imaging core, where a distal portion of the body comprises a reduced diameter single lumen segment. US 2008/0154345 describes a method and system for advancing a laser catheter across an occlusion using a catheter body having a dual lumen proximal portion and a single lumen distal portion. See also U.S. Patent Publication Nos. 2008/0172033; 2008/0009770; 2005/0245962; and U.S. Pat. Nos. 7,018,358 and 6,106,487.

BRIEF SUMMARY

The present invention overcomes some or all of the shortcomings of the prior art by providing a support catheter which comprises a catheter body having a proximal region or portion, a distal region or portion, and a single contiguous lumen extending through the proximal and distal regions. The cross-sectional area of the proximal lumen is larger than the cross-sectional area of the distal lumen so that two or more devices, such as guidewires, therapeutic catheters, imaging catheters, and most particularly cutting tip guidewires as discussed in more detail below, may be held in the proximal lumen while the distal lumen remains available for selectively advancing any one of these devices to the vasculature or other body lumen being treated. While the proximal lumen will be open, that is, there is no fixed or other barrier which defines two or more discrete lumens within the proximal lumen region, the proximal region may include structure for aligning the guidewires and catheters within the proximal lumen in order to minimize interference and tangling of such devices. Typically, the structure for aligning may comprise at least a first axial ridge disposed along at least a portion of the wall of the proximal lumen region. The ridge may be continuous or discontinuous and will be configured to confine or align the catheters, guidewires, and other elongate devices within a portion of the lumen. Usually, at least a second axial ridge will be disposed along the wall of the proximal portion of the single contiguous lumen, where the second ridge is typically but not necessarily opposite to the first axial ridge. In some instances, it may be desirable to provide at least three axial ridges in order to define at least three confinement regions within the proximal lumen portion.

The catheter body may be constructed in any conventional manner. In a first exemplary embodiment, the catheter body may be a single continuous extrusion, typically formed from conventional materials such as nylon, polyethylene, PTFE, and the like. Portions or all of the catheter body may be reinforced, e.g. with metallic braids, metal or polymeric wires, or the like.

Alternatively, the catheter body may be constructed of two, three, or more separate extrusions which are joined directly or indirectly by conventional techniques. A distal extrusion may be joined to a proximal extrusion, where the distal and proximal extrusions may be formed from different materials or the same materials having different properties and/or may have different dimensions, different reinforcement components (e.g., braid, wire, etc.), different physical characteristics, and the like. The proximal and distal extrusions may be joined directly or by an additional extrusion or other component which indirectly attaches one extrusion to an adjacent extrusion. Either or both ends of the extrusions may be flared, necked, and/or skived to facilitate attachment. The extrusions may be attached by fusing or melting the materials together, by using adhesive, by using metal or plastic connectors, or any other form of attachment. Alternatively, part of or the entire proximal portion and/or distal portion of the catheter body may be formed from nitinol or other superelastic material, typically using a nitinol hypotube, where the nitinol portion is joined to one or more polymeric region(s). Nitinol used in the proximal or distal region or portion can improve torque transmission and/or increase catheter stiffness.

The dimensions of the catheter may vary depending on intended use. For use in the coronary vasculature and smaller peripheral vessels, the catheter will typically have a length in the range from 100 cm to 180 cm, more typically in the range from 120 cm to 160 cm, with a proximal region length in the range from 70 cm to 175 cm, and a distal region length in the range from 5 cm to 30 cm, with a proximal cross-sectional area in the range from 0.2 mm$^2$ to 0.6 mm$^2$, usually from 0.3 mm$^2$ to 0.5 mm$^2$, and a distal cross-sectional area in the range from 0.1 mm$^2$ to 0.25 mm$^2$, typically from 0.11 mm$^2$ to 0.22 mm$^2$. For use in the larger vessels in the peripheral vasculature, the catheter body will typically have a length in the range from 100 cm to 150 cm, more typically in the range from 100 cm to 135 cm, with a proximal region length in the range from 80 cm to 130 cm, and a distal region length in the range from 5 cm to 30 cm, with a proximal cross-sectional area in the range from 0.6 mm$^2$ to 1.60 mm$^2$, usually from 1.25 mm$^2$ to 1.55 mm$^2$, and a distal cross-sectional area in the range from 0.25 mm$^2$ to 0.80 mm$^2$, typically from 0.62 mm$^2$ to 0.73 mm$^2$.

Methods according to the present invention comprise introducing a support catheter, such as that described above, to a target location in a body lumen. First and second elongate devices, such as guidewires, therapeutic catheters, imaging catheters, or the like, are placed in a common proximal lumen of the support catheter. Individual ones of the elongate devices are then selectively advanced, one at a time, through a distal lumen of the support catheter to the target location. The cross-sectional area of the distal lumen is less than that of the proximal lumen, allowing the support catheter to be introduced to relatively small regions of the vasculature or other body lumens.

The methods of the present invention will typically be used for crossing occlusions within a body lumen, typically a blood vessel, where the occlusion is usually total. In such methods, the first elongate device may comprise a guidewire and the second elongate device may comprise a drilling wire, such as those described in co-pending, commonly owned application Ser. Nos. 11/567,884, filed on Dec. 7, 2006; 11/636,388, filed on Dec. 7, 2006; and 11/236,703, filed on Sep. 26, 2005, the full disclosures of which are incorporated herein by reference.

While the methods of the present invention may utilize support catheters having proximal lumens which are substantially circular and free from surface features, it will often be desirable to provide means for aligning the multiple wires and devices within the common proximal lumen. For example, the walls may include one or more axial ridges or other structures or features which align the devices without fully separating the devices into separate lumens.

DETAILED DESCRIPTION

Figure 1:
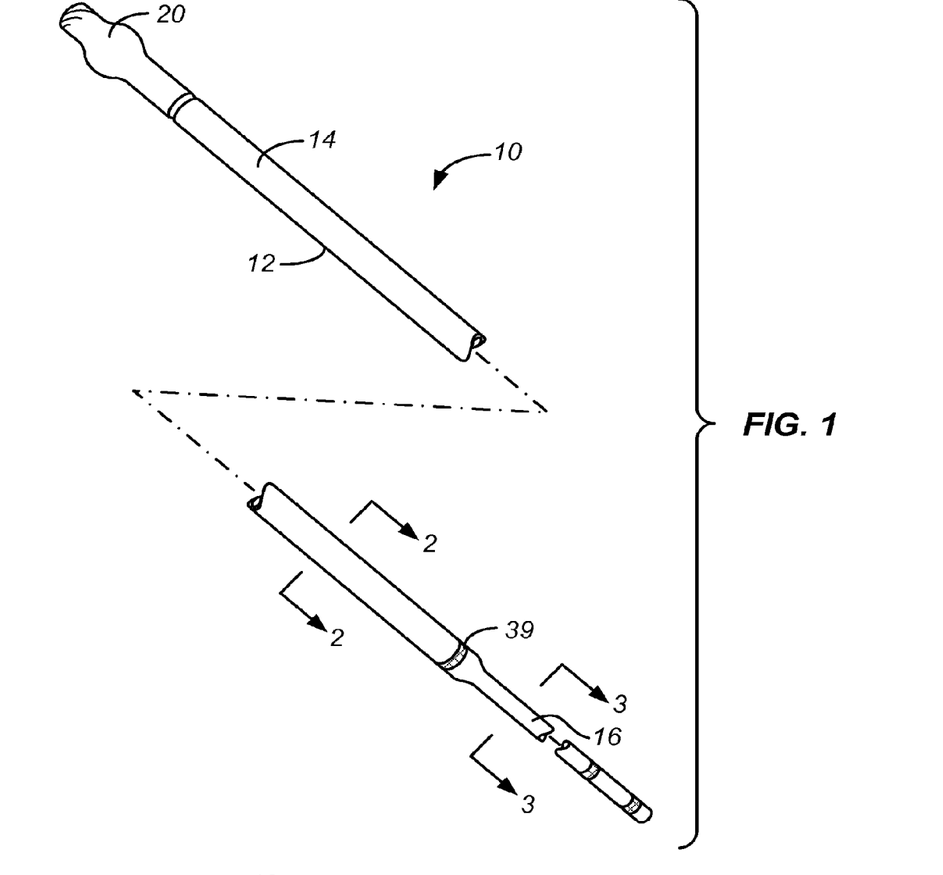
FIG. 1 is a perspective illustration of a support catheter constructed in accordance with the principles of the present invention.
Figure 2A:
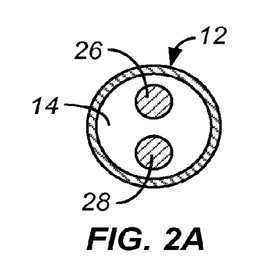
FIGS. 2A-2C are alternative cross-sectional views of a proximal region of the support catheter of the present invention taken along line 2-2 of FIG. 1.
Figure 2B:
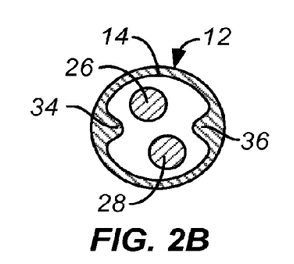
Figure 2C:
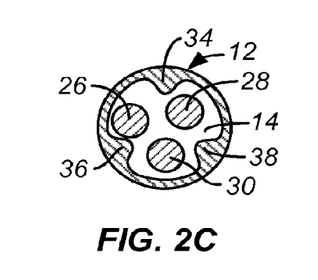
Figure 3:
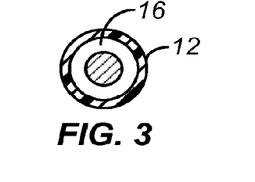
FIG. 3 is a cross-sectional view of a distal region of the support catheter of the present invention taken along line 3-3 of FIG. 1.

Referring now to FIG. 1, an exemplary support catheter 10 comprises a catheter body 12 including a proximal region or portion 14 and a distal region or portion 16. The proximal region 14 may have a variety of configurations, as shown in FIGS. 2A-2C, but it will always comprise a single open lumen which is free from walls or barriers which define isolated lumens or compartments therein. The distal region 16, as illustrated in FIG. 3, will have a cross section which is less than that of the proximal region and will usually comprise a regular or circular inner wall which is free from structure.

One or more radiopaque marker bands 39 (such as platinum, gold, tungsten, and the like) may be located at or near the distal end of the proximal portion 14 of the catheter body 12. The marker band(s) 39 allows the user to fluoroscopically image the location to which the guidewire or working device must be retracted to in order to clear the distal lumen in order to advance a different guidewire or working device. One or more radiopaque marker bands 40 (such as platinum, gold, tungsten, and the like) may also be placed at or near the distal end of the distal portion or region 16 of the catheter body 12 to allow the user to fluoroscopically image the distal end of the catheter to assist positioning the distal end at the target region in the body lumen.

The support catheter 10 will typically have a proximal hub 20 which includes one or more luer or other connectors (described in more detail with reference to FIGS. 4 and 5, below) for introducing two or more working devices, such as guidewires, therapeutic catheters, imaging catheters, and the like, into the common lumen of proximal region 14. A distal end of the proximal hub 20 may be attached to a proximal end of the proximal region with adhesive or by insert molding.

Exemplary working devices 26 and 28 are illustrated in FIGS. 2A-2C, with a third exemplary working device 30 shown in FIG. 2C. The working devices 26, 28, and 30, may, as described previously, be any elongate body or element which is desired to be introduced to a target location within the vasculature or other body lumen. Typically, for vascular applications, the working devices will be guidewires, imaging catheters, therapeutic catheters, and in the exemplary embodiments illustrated below, a drilling wire for crossing a total chronic occlusion.

After entering through the hub 20, the working devices 26 and 28 will be received within the lumen of the proximal region 14. The lumen of the proximal region 14 may be free from structure, as shown in FIG. 2A, which will be adequate for many devices which have little propensity to tangle or constrict one another. In many instances, however, it will be desirable to provide structure on the inner luminal wall of the proximal region 14 to align the working devices 26 and 28 and to inhibit the risk of tangling and interference. For example, as shown in FIG. 2B, axial ridges 34 and 36 may be formed along the inner luminal wall, typically opposed at 180.degree., in order to partially confine the working devices 26 and 28 within upper and lower regions of the lumen. It would also be possible to provide a third axial ridge 38 or more, as illustrated in FIG. 2C. Since only one working device at a time will be introduced into the distal region, it will usually be unnecessary to provide any surface features or other elements along the inner rim of the walls of the distal region.

Figure 4:
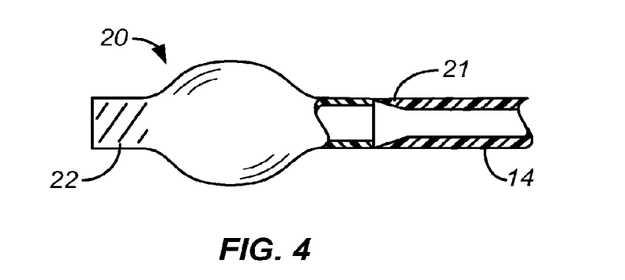
FIG. 4 illustrates a single ported hub as shown in FIG. 1.
Figure 5:
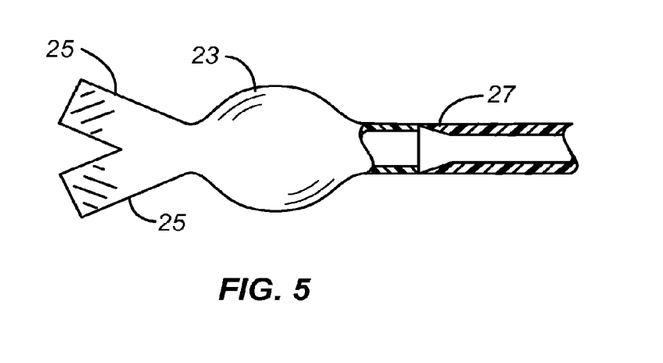
FIG. 5 illustrates an alternative hub construction with two ports.

The hub 20 and the proximal end of proximal portion 14 may be configured to facilitate the transition of multiple working devices into the single open lumen, often being tapered. The hub 20 may also have one, two, or more separate luer or other connectors for simultaneously receiving the multiple working devices. As illustrated in FIG. 4, the hub 20 includes only a single luer connector 22 which can receive two or more working devices. The proximal end of the proximal region 14 of the catheter body has a taper or counter sink 21 in the inner diameter. The taper 21 allows the multiple working devices to self-align between the ridges (when present). Referring now to FIG. 5, an alternative hub 23 hub includes two ports 25 (such as luer connectors) for separately introducing working devices, such as guidewires, therapeutic catheters, imaging catheters, and the like, into the common lumen of proximal region 14. Alternatively, one port 25 may be used for introducing two or more working devices and the second port 25 may be used for flushing the catheter lumen with saline or injecting contrast into the lumen without having to remove the working devices. A taper or counter sink 27 is provided to assist in alignment as described above.

Figure 6A:
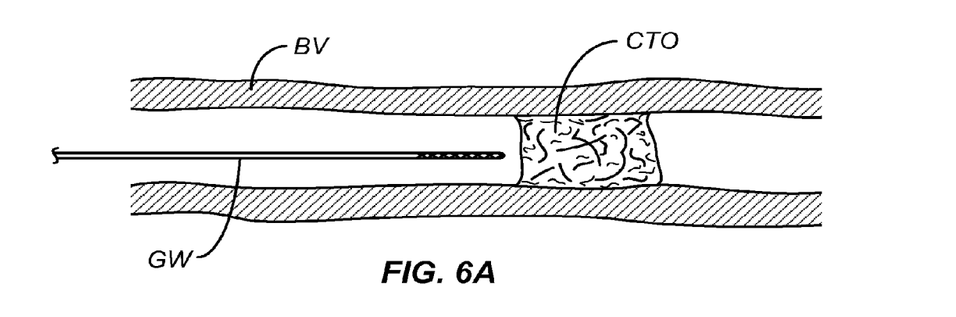
FIGS. 6A-6I illustrate an exemplary method of the present invention using the support catheter of FIG. 1 for selectively deploying a guidewire and a drill wire to cross a total occlusion in a blood vessel.
Figure 6B:
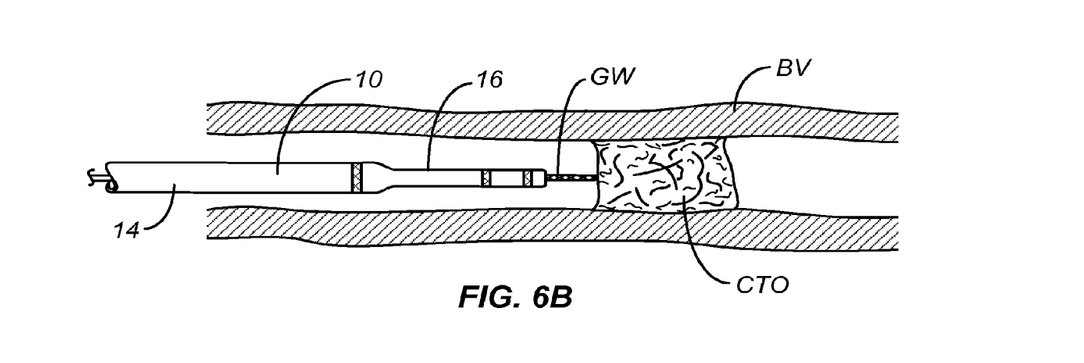

Referring now to FIGS. 6A-6H, a method utilizing the support catheter 10 of the present invention for introducing a conventional guidewire and drilling wire to cross a total chronic occlusion in the vasculature will be described. As shown in FIG. 6A, a conventional guidewire GW is introduced through the lumen of a blood vessel BV to a proximal side of a chronic total occlusion CTO. The support catheter 10 is then introduced over the guidewire so that the distal region 16 approaches the proximal side of the chronic total occlusion CTO, as shown in FIG. 6B. The proximal portion of the guidewire GW will pass through the single lumen of the proximal region 14 of the support catheter and externally through the hub 20 (FIG. 1).

Figure 6C:
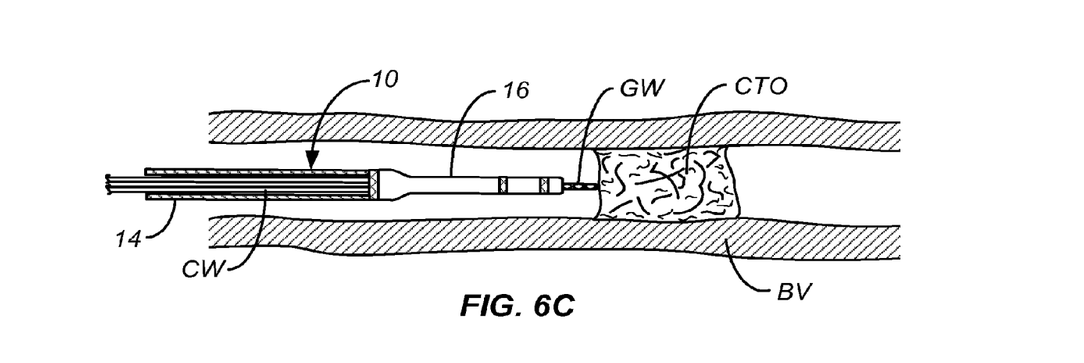
Figure 6D:
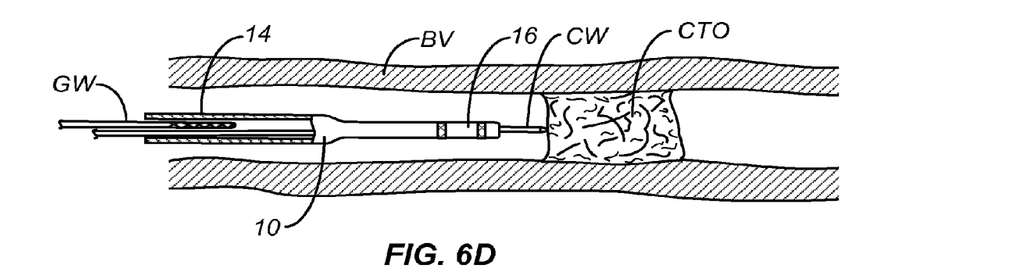
Figure 6E:
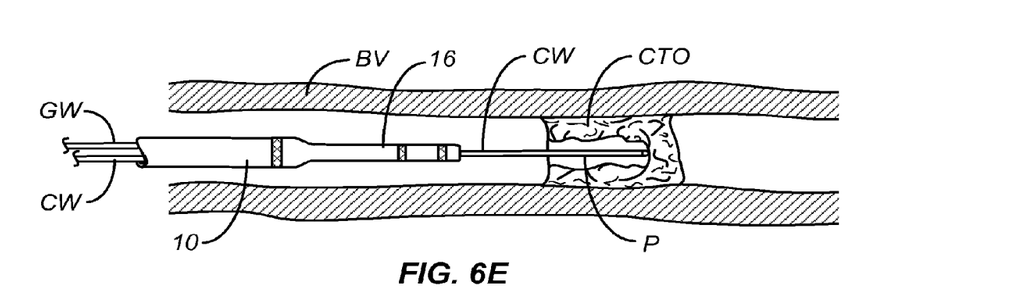
Figure 6F:
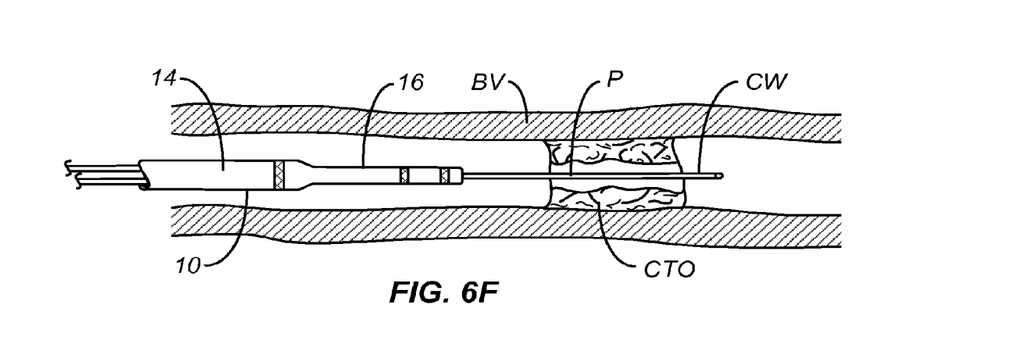
Figure 6G:
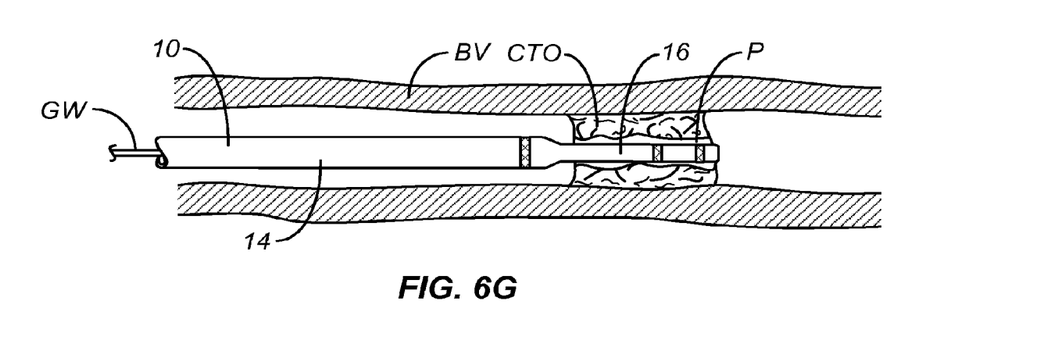
Figure 6H:
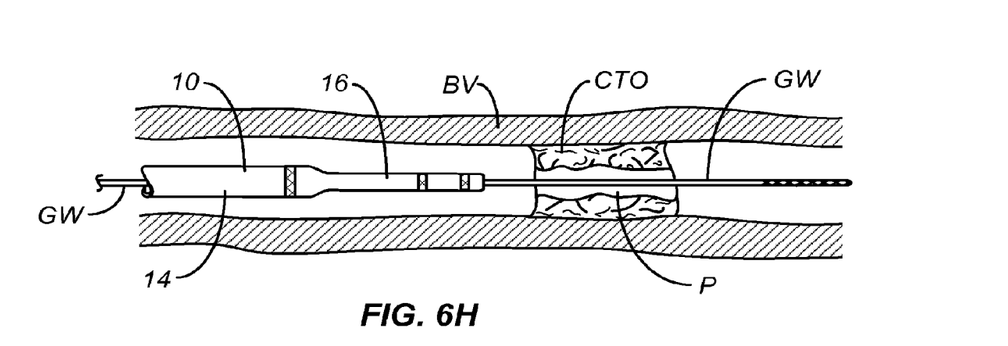
Figure 6I:
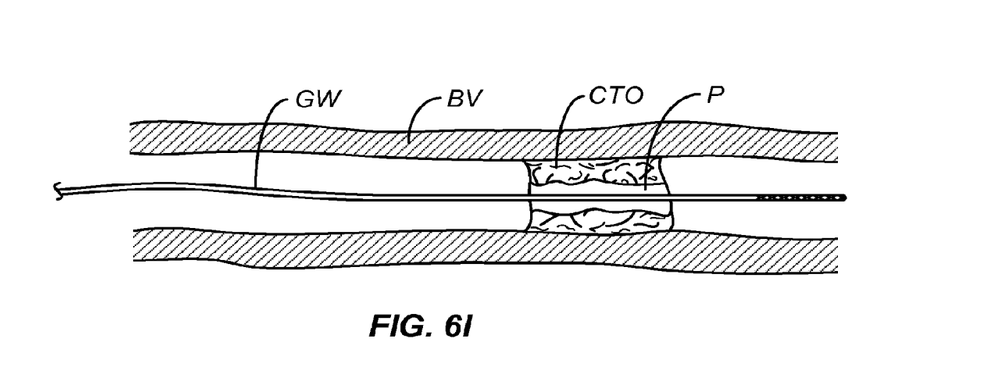

After the support catheter 10 has been properly positioned proximate the chronic total occlusion CTO, as shown in FIG. 6C, a cutting guidewire CW may be introduced through the other hub 20 (FIG. 1) and advanced through the single lumen of the proximal portion 14. After the cutting wire CW is positioned just proximally of the distal region 16, as shown in FIG. 6C, the guidewire may be withdrawn proximally and stowed in the lumen of the proximal portion 14, as shown in FIG. 6D, while the cutting wire CW is advanced distally through the distal portion 16 to engage a proximal surface of the chronic total occlusion CTO. The cutting wire may then be activated, as shown in the co-pending applications previously incorporated herein by reference, and advanced through the chronic total occlusion CTO, as shown in FIG. 6E, until the cutting wire fully penetrates the occlusion, as shown in FIG. 6F. After the passage P has been formed in the chronic total occlusion CTO, the support catheter 10 may be advanced distal to the chronic total occlusion CTO, and the cutting wire CW may be withdrawn as shown in FIG. 6G. The guidewire GW can then be advanced from the proximal portion 14 through the distal portion 16 and exit distal to the chronic total occlusion CTO, as shown in FIG. 6H. By then withdrawing the support catheter 10, as shown in FIG. 6I, the guidewire is in place through the chronic total occlusion chronic total occlusion CTO allowing for the introduction of additional therapeutic catheters, such as angioplasty catheters, atherectomy catheters, stent placement catheters, drug delivery catheters, and the like. Alternatively, the cutting wire may be proximally retracted and optionally withdrawn from the support catheter. The guidewire GW may then be advanced from the proximal portion 14, through the distal portion 16, and ultimately through the passage P, allowing the support catheter to be withdrawn leaving the guidewire in place across the chronic total occlusion CTO, as shown in FIG. 6I.

While the above is a complete description of the preferred embodiments of the invention, various alternatives, modifications, and equivalents may be used. Therefore, the above description should not be taken as limiting the scope of the invention which is defined by the appended claims.

What is claimed:

1. A method of crossing an occlusion in a blood vessel, comprising:
    advancing a guidewire through a lumen of a blood vessel to a location proximal of an occlusion;
    advancing an exchange catheter over the guidewire to position a distal end of the exchange catheter proximal of the occlusion, the exchange catheter including a catheter body having a single contiguous lumen with a proximal portion through a proximal region of the catheter body and a distal portion through a distal region of the catheter body, the exchange catheter advancing over the guidewire with the guidewire within the single contiguous lumen;
    withdrawing the guidewire into the exchange catheter such that the guidewire is positioned within the proximal portion of the single contiguous lumen;
    advancing a cutting wire into and through the distal portion of the single contiguous lumen and out of the distal end of the exchange catheter with the guidewire located in the proximal region of the catheter body; and
    forming a passage through the occlusion with the cutting wire;
    wherein the single contiguous lumen is configured to accommodate the guidewire and the cutting wire simultaneously within the proximal portion of the single contiguous lumen and only accommodate one of the guidewire and the cutting wire at a time within the distal portion of the contiguous lumen.

2. The method of claim 1, further comprising:
    advancing the exchange catheter through the passage formed through the occlusion.

3. The method of claim 2, further comprising:
    withdrawing the cutting wire into the proximal portion of the single contiguous lumen after forming the passage; and
    thereafter, advancing the guidewire through the distal portion of the single contiguous lumen and out of the distal end of the exchange catheter to a location distal of the occlusion.

4. The method of claim 3, further comprising:
    advancing an angioplasty catheter over the guidewire to the occlusion.

5. The method of claim 3, further comprising:
    advancing a stent placement catheter over the guidewire to the occlusion.

6. The method of claim 1, wherein the cutting wire is positioned in the proximal portion of the single contiguous lumen of the exchange catheter when the guidewire is positioned in the distal portion of the single contiguous lumen of the exchange catheter.

7. The method of claim 1, wherein the guidewire is positioned in the proximal portion of the single contiguous lumen of the exchange catheter when the cutting wire is positioned in the distal portion of the single contiguous lumen of the exchange catheter.

8. A method of crossing an occlusion in a blood vessel, comprising:
    advancing a guidewire through a lumen of a blood vessel to a location proximal of an occlusion;
    advancing an exchange catheter over the guidewire to position a distal end of the exchange catheter proximal of the occlusion, the exchange catheter including a proximal region and a distal region, with a single contiguous lumen extending through the proximal and distal regions, the single contiguous lumen having a proximal portion through the proximal region and a distal portion through the distal region;

withdrawing the guidewire into the proximal portion of the single contiguous lumen of the exchange catheter;

advancing a cutting wire through the distal portion of the single contiguous lumen and out of the distal end of the exchange catheter with the guidewire located in the proximal portion of the single contiguous lumen; and forming a passage through the occlusion with the cutting wire;

wherein the proximal portion of the single contiguous lumen of the exchange catheter is sized to receive the cutting wire and the guidewire simultaneously while the distal portion of the single contiguous lumen of the exchange catheter is sized to receive only one of the cutting wire and the guidewire at a time.

9. The method of claim 8, further comprising:

advancing the exchange catheter through the passage formed through the occlusion.

10. The method of claim 9, further comprising:

withdrawing the cutting wire into the proximal portion of the single contiguous lumen of the exchange catheter after forming the passage; and thereafter, advancing the guidewire through the distal portion of the single contiguous lumen and out of the distal end of the exchange catheter to a location distal of the occlusion.

11. The method of claim 10, further comprising:

advancing an angioplasty catheter over the guidewire to the occlusion.

12. The method of claim 10, further comprising:

advancing a stent placement catheter over the guidewire to the occlusion.

13. The method of claim 8, wherein the proximal region and the distal region of the exchange catheter are advanced into the blood vessel.

* * * * *